United States Patent [19]

Murao et al.

[11] Patent Number: 5,969,175

[45] Date of Patent: Oct. 19, 1999

[54] PURIFICATION OF NITRILE

[75] Inventors: Kouzo Murao; Katsuo Ishii; Tetsuro Horinouchi, all of Kanagawa, Japan

[73] Assignee: Mitsubishi Rayon Co., Ltd., Tokyo, Japan

[21] Appl. No.: 08/874,727

[22] Filed: Jun. 13, 1997

[30] Foreign Application Priority Data

Jun. 20, 1996 [JP] Japan ................................ 8-178696

[51] Int. Cl.$^6$ .................................................. C07C 255/00
[52] U.S. Cl. ............................................ 558/411; 558/462
[58] Field of Search ..................................... 558/411, 462

[56] References Cited

U.S. PATENT DOCUMENTS 3,541,131  11/1970  Darcas et al. ........................... 558/464

FOREIGN PATENT DOCUMENTS

| 217 212 A1 | 1/1985 | Germany | ..................... C07C 121/18 |
| 57-62247 | 4/1982 | Japan | ........................... C07C 121/32 |
| 57-26586 | 6/1982 | Japan | ......................... C07C 103/133 |
| 58-1108 | 1/1983 | Japan | ........................... C07C 121/32 |
| 58-134063 | 8/1983 | Japan | ......................... C07C 103/133 |
| 2114118 | 8/1983 | United Kingdom . | |

*Primary Examiner*—Johann Richter
*Assistant Examiner*—Joseph Murray
*Attorney, Agent, or Firm*—Sughrue, Mion, Zinn, Macpeak & Seas, PLLC

[57] ABSTRACT

A method for purifying a nitrile which comprises contacting a nitrile containing an aldehyde with a cation exchange resin carrying a polyamine to remove the aldehyde from the nitrile. The ion exchange resin can be regenerated and reused repeatedly.

16 Claims, No Drawings

PURIFICATION OF NITRILE

FIELD OF THE INVENTION

This invention relates to a method for purifying a nitrile, and more particularly, to a method for removing trace amounts of an aldehyde from a nitrile efficiently and economically.

BACKGROUND OF THE INVENTION

Nitriles, and particularly aliphatic nitrites, are obtained by the ammoxydation of olefins. Nitriles thus obtained inevitably contain a trace amount of an aldehyde as an impurity, which contaminates the system during the step of recovering the nitrile or in coloring the product nitrile. Furthermore, recent developments in chemical technology require higher purity nitrites. However, the volatility of a nitrile is often close to that of an aldehyde present therein as an impurity. Thus, the separation of these components by distillation is uneconomical, and requires many plates and a considerable amount of energy. Therefore, there is a need in the art to develop an efficient method for removing an aldehyde impurity from a nitrile.

Several proposals have been made to date including, for example, a method of adding sodium hydrogennitrite to methacrylonitrile to remove methacrolein in the form of an addition salt (see JP-A-57-62247, the term "JP-A" as used herein means an "unexamined published Japanese patent application"), a method of adding acetylacetone, etc. to acrylonitrile and removing the reaction product between the acetylacetone and acrolein by distillation or like means (see JP-B-57-26586, the term "JP-B" as used herein means an "examined published Japanese patent application"), and a method of using ozone for removing acrolein from acetonitrile (see DD 217212).

Methods of using an ion exchange resin for removing acrolein from acrylonitrile have also been proposed. For example, the use of a porous anion exchange resin having a primary amino group and/or a secondary amino group as an ion exchange group (see JP-B-58-1108) or an anion exchange resin gel (see JP-A-58-134063) is known. These methods show promise for specifically removing aldehydes without producing other impurities in the system.

However, according to the method of using an anion exchange resin having a primary amino group and/or a secondary amino group as an ion exchange group, the amino group and the aldehyde group undergo an amino-carbonyl reaction to form a covalent bond. Thus, the aldehyde group cannot be released in a usual manner. As a result, the spent ion exchange resin is hardly regenerated and must be discarded, thus adding the cost of disposal to this process.

SUMMARY OF THE INVENTION

It is therefore an object of the present invention to provide a method for removing an aldehyde from a nitrile by using an ion exchange resin that can be regenerated and repeatedly used.

As a result of extensive study, the present inventors have found a cation exchange resin carrying a polyamine that is extremely effective in removing an aldehyde from a nitrile to thereby achieve the present invention.

The present invention provides a method of purifying a nitrile which comprises contacting a nitrile containing an aldehyde with a cation exchange resin carrying a polyamine to remove the aldehyde from the nitrile.

DETAILED DESCRIPTION OF THE INVENTION

The cation exchange resin for use in the present invention is not particularly limited. Examples of suitable cation exchange resins are porous or highly porous (micro-reticulated) ones, such as the DIAION PK and HPK series resins (produced by Mitsubishi Chemical Co., Ltd.); the Amberlyst series resins (produced by Japan Organo Co., Ltd.); Amberlite 200C(P and T), XT-1024 and 252, IRC-50, and HX-204 (all produced by Japan Organo Co., Ltd.); and Duolite C-26 and 265 (both produced by Sumitomo Chemical Co., Ltd.). These commercially available cation exchange resins may be used as such, or after washing with water, or after pretreating with an aqueous acid solution followed by washing with water.

The polyamines supported on the cation exchange resin include ethylenediamine, diethylenetriamine, triethylenetetramine, tetraethylenepentamine, 1,3-propanediamine, 1,4-butanediamine, 1,6-hexamethylenediamine, guanidine and hydrazine. Of these, ethylenediamine, diethylenetriamine, triethylenetetramine, 1,3-propanediamine and hydrazine are preferred. These polyamines can be used either individually or as a combination of two or more thereof.

The nitrile to be treated in accordance with the method of the present invention includes aliphatic nitrites and aromatic nitrites. Specific examples thereof are aliphatic nitriles having 2 to 4 carbon atoms, e.g., acrylonitrile, methacrylonitrile, acetonitrile, and propionitrile; and aromatic nitrites, e.g., benzonitrile. Aldehyde impurities that are present in these nitrites and that are removed by the method of the present invention include acrolein, methacrolein, acetaldehyde, propionaldehyde and benzaldehyde.

According to the method of the present invention, a nitrile containing an aldehyde (generally in an amount of 1 to 10 ppm) can be efficiently purified to reduce the aldehyde concentration of the nitrile to less than 1 ppm.

The present invention manifests its pronounced effect particularly when applied to a nitrile containing an aldehyde whose volatility is close to that of the nitrile.

By following the method of the present invention, not only an aldehyde but other carbonyl compounds reactive with an amino group, such as carboxylic acids and ketones, can be removed concomitantly. The method of the present invention is applicable not only to nitrites, but also to solvents containing an aldehyde, etc.

The polyamine is supported on the ion exchange resin, for example, by continuously contacting the ion exchange resin with an aqueous solution of the polyamine either batchwise or continuously. The concentration of the polyamine aqueous solution is usually from 0.01M to its saturation concentration. For good workability, the concentration is preferably from 0.1 to 5M.

Contact of a nitrile with the cation exchange resin having a polyamine supported thereon can be carried out batchwise or continuously by using a fixed bed, a mobile bed or a fluidized bed. For economical and operational reasons, column operation using an ion exchange column (i.e., a fixed bed) is recommended. In this case, while the flow rate of a nitrile depends on the aldehyde concentration of the nitrile and the desired degree of aldehyde removal, the amount of the nitrile thus treated is desirably not more than 100 times the volume of the resin per one hour.

After aldehyde removal, the spent ion exchange resin can be regenerated with great ease. That is, a Schiff base, which has been produced by the amino-carbonyl reaction between the polyamine supported on the ion exchange resin and an aldehyde in the nitrile, can be easily released from the resin by a generally employed method for regenerating cation exchange resins, i.e., by contacting the resin with an aqueous acid solution followed by thoroughly washing with water.

According to the present invention, the polyamine supported on an ion exchange resin is easily released from the resin by a generally employed method for regenerating cation exchange resins. Therefore, the present invention makes it possible to repeat the steps of bonding a polyamine to the ion exchange resin, carrying out an amino-carbonyl reaction between an aldehyde as an impurity of a nitrile and the amino group bonded to the ion exchange resin, and repeatedly regenerating the spent ion exchange resin having no aldehyde removing ability, to thereby efficiently purify a nitrile.

The present invention is illustrated in greater detail below with reference to the following Examples, but it should be understood that the present invention is not to be construed as being limited thereto.

EXAMPLES 1 TO 5 AND COMPARATIVE EXAMPLE 1

Ten milliliters of a strongly acidic ion exchange resin Amberlyst 15WET (produced by Japan Organo Co., Ltd.) was packed into each of three glass columns. A 1M aqueous solution of the polyamine shown in Table 1 below was passed through the column in a down-flow system at room temperature at a rate of 10 ml/hr for 4 hours, to thereby support the amine on the ion exchange resin.

Industrial acrylonitrile having an acrolein content of 5 ppm, industrial methacrylonitrile having a methacrolein content of 5 ppm, and industrial acetonitrile having an acetaldehyde content of 5 ppm were each passed through the respective columns in a down-flow system at a flow rate of 10 ml/hr. After passing these nitriles through the respective columns for 3 days, a sample (a nitrile compound) was taken from the effluent of each column and analyzed using a capillary gas chromatograph (HP-5890 II, manufactured by Hewlett-Packard Company; column: DB225, produced by J & W) to determine the aldehyde concentration of the eluate.

For comparison, the same nitriles were treated in the same manner as described above, except for using Amberlyst 15WET not carrying a polyamine.

The results thus obtained are shown in Table 1.

TABLE 1

| Example No. | Polyamine | Acrolein Concn. in Acrylonitrile (ppm) | Methacrolein Concn. in Methacrylonitrile (ppm) | Acetaldehyde Concn. in Acetonitrile (ppm) |
|---|---|---|---|---|
| Example 1 | ethylenediamine | <0.5 | <0.5 | <0.5 |
| Example 2 | diethylenetriamine | <0.5 | <0.5 | <0.5 |
| Example 3 | triethylenetetramine | <0.5 | <0.5 | <0.5 |
| Example 4 | 1,3-propanediamine | <0.5 | <0.5 | <0.5 |
| Example 5 | hydrazine | <0.5 | <0.5 | <0.5 |
| Compara. Example 1 | none | 5.0 | 5.0 | 5.0 |

EXAMPLE 6 AND COMPARATIVE EXAMPLE 2

Ten milliliters of Amberlyst 35WET (produced by Japan Organo Co., Ltd.) was charged into a glass column. Then, a 1M aqueous solution of diethylenetriamine was passed therethrough at a rate of 10 ml/hr for 4 hours, to thereby support the amine on the ion exchange resin. The column was thoroughly washed with 1 l of distilled water. The water remaining in the column was removed by passing acrolein-free acrylonitrile therethrough. Thereafter, 50 l of acrylonitrile containing 5 ppm of acrolein was passed through the column in a down-flow system at a rate of 400 ml/hr.

After the above treatment, the ion exchange resin was back washed with 1 l of distilled water in an up-flow system, and 1 l of a 1N sulfuric acid aqueous solution was then passed through the column at a rate of 100 ml/hr to regenerate the ion exchange resin. The resin was again treated with diethylenetriamine, and acrylonitrile was passed therethrough in the same manner as described above.

The above-described steps of regenerating the ion-exchange resin and passing acrylonitrile therethrough were repeated 8 more times (10 total passes). The acrolein concentration of the eluate was measured for each pass in the same manner as in Examples 1 to 5.

For comparison, acrylonitrile was repeatedly passed through the column without regenerating the ion exchange resin after each pass, and the acrolein concentration of the eluate was measured for each pass. The results obtained are shown in Table 2 below.

TABLE 2

| | | Acrolein Concn. (ppm) Number of Repetitions | | | | |
|---|---|---|---|---|---|---|
| Example No. | Regeneration | 0 | 1 | 2 | 3–8 | 9 |
| Example 6 | yes | <0.5 | <0.5 | <0.5 | <0.5 | <0.5 |
| Compara. Example 2 | no | <0.5 | 4.5 | 5.0 | 5.0 | 5.0 |

EXAMPLES 7 TO 11

Ten milliliters each of DIAION 228LH, Amberlyst 16WET, and Amberlite IRC-50 were placed into respective test tubes and washed with pure water. To each test tube were added 30 ml of a 1M hydrazine aqueous solution, and the test tubs were shaken at temperature for 1 day. The ion-exchange resin was washed an aldehyde-free nitrile. Then, 30 ml of an aldehyde-containing nitrile shown in Table 3 below was added to the test tube, followed by shaking for 2 hours. The aldehyde concentration of the nitrile was measured in the same manner as in Examples 1 to 5.

The aldehyde concentrations before and after the ion-exchange treatment are shown in Table 3 below.

TABLE 3

| Example No. | Ion Exchange Resin | Nitrile | Aldehyde | Aldehyde Concn. (ppm) Before Treatment | After Treatment |
|---|---|---|---|---|---|
| 7 | DIAION 228LH | acrylonitrile | acrolein | 1000 | <1 |
| 8 | DIAION 228LH | methacrylonitrile | methacrolein | 200 | 20 |
| 9 | DIAION 228LH | acetonitrile | acetaldehyde | 200 | 10 |
| 10 | Amberlyst 16WET | acrylonitrile | acrolein | 1000 | <1 |
| 11 | Amberlite IRC-50 | acrylonitrile | acrolein | 1000 | <1 |

While the invention has been described in detail and with reference to specific examples thereof, it will be apparent to one skilled in the art that various changes and modifications can be made therein without departing from the spirit and scope thereof.

What is claimed is:

1. A method for purifying a nitrile which comprises contacting a nitrile containing an aldehyde with a cation exchange resin carrying a polyamine to remove the aldehyde from the nitrile.

2. The method according to claim 1, wherein said nitrile contains from 2 to 4 carbon atoms.

3. The method according to claim 1, wherein said polyamine is selected from the group consisting of ethylenediamine, diethylenetriamine, triethylenetetramine, 1,3-propanediamine and hydrazine.

4. The method according to claim 1, wherein said nitrile is selected from the group consisting of aliphatic nitriles having from 2 to 4 carbon atoms and aromatic nitrites.

5. The method according to claim 1, wherein said aldehyde is selected from the group consisting of acrolein, methacrolein, acetaldehyde, propionaldehyde and benzaldehyde.

6. The method according to claim 1, wherein the nitrile after contacting with the cation exchange resin contains said aldehyde in an amount of less than 1 ppm.

7. A method for purifying a nitrile which comprises the steps of:

(1) contacting a nitrile containing an aldehyde with a cation exchange resin having a polyamine supported thereon;

(2) regenerating the cation exchange resin of step (1); and (3) repeating step (1) using the regenerated cation exchange resin.

8. The method according to claim 7, wherein said contacting step comprises continuously contacting said nitrile containing an aldehyde with a cation exchange resin having a polyamine supported thereon.

9. The method according to claim 7, wherein said contacting step comprises batchwise contacting said nitrile containing an aldehyde with a cation exchange resin having a polyamine supported thereon.

10. The method according to claim 7, which further comprises repeating steps (1) and (2) a plurality of times using the regenerated cation exchange resin.

11. The method according to claim 7, wherein said regenerating comprises contacting the cation exchange resin with an aqueous acid solution followed by washing with water.

12. The method according to claim 11, which further comprises contacting the regenerated cation exchange resin with an aqueous solution of the polyamine.

13. The method according to claim 7, wherein said polyamine is selected from the group consisting of ethylenediamine, diethylenetriamine, triethylenetetramine, 1,3-propanediamine and hydrazine.

14. The method according to claim 7, wherein said nitrile is selected from the group consisting of aliphatic nitrites having from 2 to 4 carbon atoms and aromatic nitrites.

15. The method according to claim 7, wherein said aldehyde is selected from the group consisting of acrolein, methacrolein, acetaldehyde, propionaldehyde and benzaldehyde.

16. The method according to claim 7, wherein the nitrile after contacting with the cation exchange resin contains said aldehyde in an amount of less than 1 ppm.

* * * * *